(12) United States Patent
Misch

(10) Patent No.: US 8,118,597 B2
(45) Date of Patent: Feb. 21, 2012

(54) LATERALLY INSERTED DENTAL IMPLANT ASSEMBLY AND METHOD FOR SECURING A DENTAL PROSTHESIS

(76) Inventor: Carl E. Misch, Birmingham, MI (US)

(*) Notice: Subject to any disclaimer, the term of this patent is extended or adjusted under 35 U.S.C. 154(b) by 124 days.

(21) Appl. No.: 12/468,522

(22) Filed: May 19, 2009

(65) Prior Publication Data

US 2010/0297584 A1  Nov. 25, 2010

(51) Int. Cl.
*A61C 8/00* (2006.01)
(52) U.S. Cl. .......................... 433/176; 433/173
(58) Field of Classification Search .................. 433/173, 433/176
See application file for complete search history.

(56) References Cited

U.S. PATENT DOCUMENTS

| | | | |
|---|---|---|---|
| 3,919,772 A * | 11/1975 | Lenczycki | 433/173 |
| 3,925,892 A * | 12/1975 | Juillet | 433/176 |
| 4,516,937 A * | 5/1985 | Bosker | 433/173 |
| 4,722,687 A | 2/1988 | Scortecci | |
| 4,789,337 A | 12/1988 | Scortecci | |
| 4,815,974 A | 3/1989 | Scortecci | |
| 4,842,517 A * | 6/1989 | Kawahara et al. | 433/173 |
| 4,964,801 A * | 10/1990 | Kawahara et al. | 433/173 |
| 5,306,149 A * | 4/1994 | Schmid et al. | 433/173 |
| 5,312,256 A | 5/1994 | Scortecci | |
| 5,320,529 A | 6/1994 | Pompa | |
| 5,433,607 A * | 7/1995 | Schmid et al. | 433/173 |
| 5,927,979 A | 7/1999 | Misch | |
| 6,068,480 A | 5/2000 | Misch | |
| 6,083,004 A | 7/2000 | Misch | |
| 6,402,516 B2 | 6/2002 | Ihde | |
| 6,863,529 B2 | 3/2005 | Strong | |
| 6,991,463 B2 | 1/2006 | Ihde | |

FOREIGN PATENT DOCUMENTS

EP  0 935 949 A1 * 8/1999
FR  2 302 715    * 10/1976

* cited by examiner

*Primary Examiner* — Ralph Lewis
(74) *Attorney, Agent, or Firm* — Brooks Kushman P.C.

(57) ABSTRACT

A dental implant assembly kit and method for insertion into a bone, the assembly serving to support a dental prosthesis or other dental structure. The assembly includes a base plate having a bone-facing surface and a pillar-supporting surface that defines an off-center region; a ledge depending from the bone-facing surface of the basal plate; and a pillar extending from the off-center region of the pillar-supporting surface of the basal plate.

12 Claims, 4 Drawing Sheets

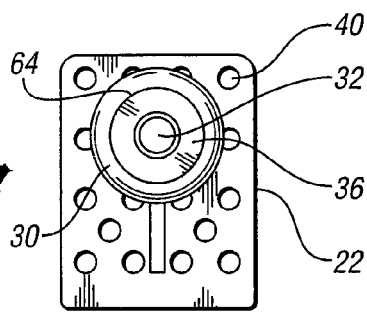
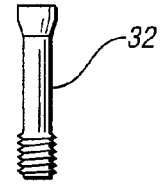
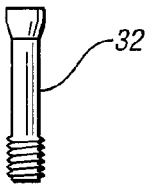
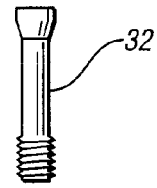
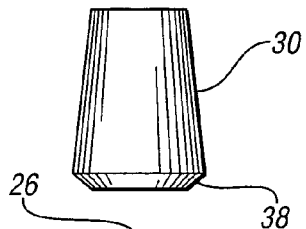
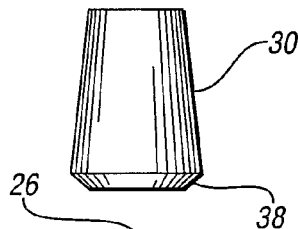
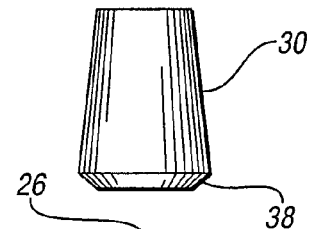
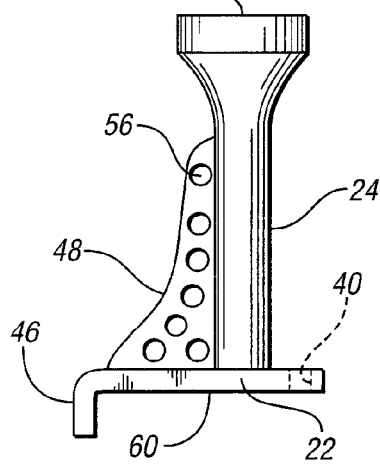
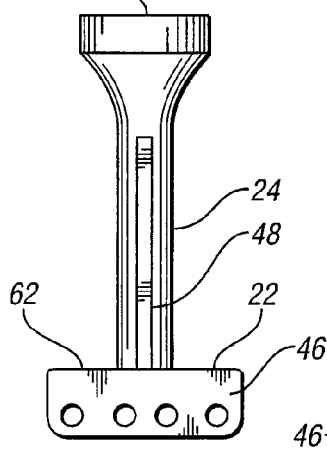
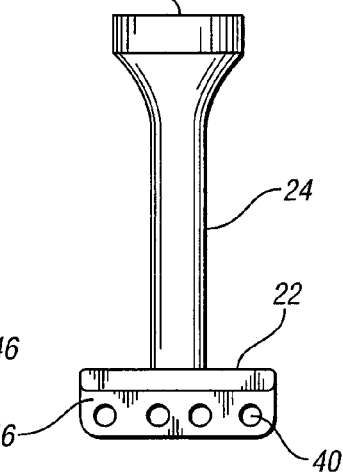
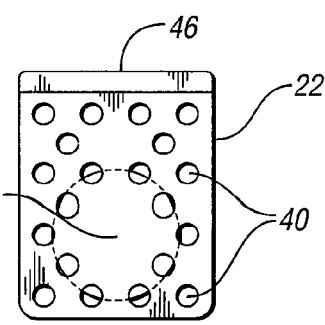

LATERALLY INSERTED DENTAL IMPLANT ASSEMBLY AND METHOD FOR SECURING A DENTAL PROSTHESIS

BACKGROUND OF THE INVENTION

1. Field of the Invention

The invention relates to a surgically implanted, laterally inserted dental implant assembly that is placed surgically within the mandibular or maxillary bone to support and provide resistance to displacement of a dental prosthesis, its method of implantation, and a related kit that includes a cutting tool and an implant assembly.

2. Background Art

Modern dentistry recognizes that functions of the masticatory system are best achieved by conserving and protecting remaining hard and soft tissues. For some patients, the loss of even a few teeth is traumatic. There is a strong incentive to seek dental care to preserve and restore normal speech, masticatory function, and a socially acceptable appearance. Dental implants have been developed in response to these needs.

Implant-supported fixed prostheses offer several advantages: avoidance of soft-tissue and implant trauma avoidance of bone complications caused by implant mobilization during mastication optimum fit at the bone-implant interface since the bone adapts immediately after implant placement and subsequent installation of the fixed prosthetic tooth. Such implants have been known to function well under various physiological conditions—normal food intake, which helps the body and peri-implant tissues to heal faster, stimulation of blood supply and drainage: avoidance of venous stasis, normal speech and resumption of socio-professional activities, and increased patient self-confidence.

But post-type implants and the way they are positioned have drawbacks. The boring of the bone in a vertical plane is necessarily deep to accommodate the height of the implant. But the bone may not have sufficient height. Also, the implant cannot easily pass round such obstacles as sinuses, nasal fossae, nerves, because boring is almost always done vertically.

Moreover, such implants, when inserted vertically are subject to the transmission of the forces imposed on them by mastication. They work essentially on an edge and have a strong tendency to self-bore under chewing or tooth-grinding pressures. Consequently these types of known post-type implants cannot be adapted to all bony structures.

In positioning a dental implant, it is desirable to seat the implant securely into the bone. Even the slightest mobility of the implant inside the bone often leads to ultimate rejection.

Conventionally, once the implant is set into the bone, a tapped ring or screw is set onto the outside part of the implant, which is generally a threaded rod. Onto this tapped ring or screw, a dental prosthesis is fixed, usually with a cement.

With a laterally inserted dental implant, osteotomy is initiated on the buccal or lingual/palatal aspect of the jaw. (Scortecci, Mich et al., "IMPLANTS AND RESTORATIVE DENTISTRY", p. 5 (2001).) Such implants are exemplified by the T3D implant developed by Juillet (1972) and the Diskimplant® (Scortecci, 1984). The Diskimplant® requires a specific instrument for osteotomy—a cutter manufactured of titanium. The Diskimplant® combines a horizontal disk and a post. See, e.g., U.S. Pat. No. 4,789,337, which is incorporated herein by reference.

A cutter is used to prepare the lateral bone incision from one cortical layer to the other. The minimally larger implant is then impacted into the bone receptor site. Close contact at the bone-implant interface encourages immediate primary retention. A wide range of base diameters and column heights allows the surgeon to make optimal use of all available bone in both horizontal and vertical dimensions.

One advantage of such approaches is that the placement of laterally inserted implants eliminates the need for reduction of thin premaxillary ridges, in contrast to conventional screw-type implants. Subsequent crestal bone loss and gingival retraction are thus less severe and often nonexistent. As a result, a better aesthetic outcome is achieved without systematic grafting.

Such disk-column implants represent a possible solution for patients with small bone volumes. The technique can also be used to salvage situations in which an implant and/or graft have failed. Stresses are concentrated primarily at the base of the disk.

However, one of the weaknesses of conventional disk-column systems, is that the column or post that lies in the center of the disk and is relatively small in diameter. Not infrequently, fracture of the implant is often the result. Such implants, inserted in a lateral direction often break under the stresses imposed during insertion or in use. One problem of conventional approaches is that the post is often too facial to the natural tooth position in the mandible and too palatal in the maxilla.

A related problem with conventional disk-column techniques is that if the hole is oversized, or if the underlying bone is soft, the implant is not fixed securely after insertion.

The prior art is also exemplified by U.S. Pat. Nos. 4,722,687 and 4,815,974.

SUMMARY OF THE INVENTION

In one embodiment, a dental implant assembly has a base plate having a bone-facing surface and a pillar-supporting surface that defines an off-center region; a ledge depending from the bone-facing surface of the basal plate at an angle theta; and a pillar extending from the off-center region of the pillar-supporting surface of the basal plate.

The disclosed implant allows a dental surgeon, in a wide variety of osteal environments, to replace the natural pillars of one or more teeth by plate-supported mechanical pillars that are placed either into the mandible or the maxilla.

The buttress is provided in the same plane as the pillar to support the pillar in relation to the jaw bone and in relation to the base plate. The buttress acts not only as an anti-rotational element, but also facilitates the step of implanting the assembly into the bone.

In the present invention, the pillar is off-center so it is in the position of a natural tooth, even though the bone is reabsorbed in height and/or width.

Thus, one object of the invention is to provide a dental implant assembly with a disk and a buttressed pillar that is firmly affixed thereto and thus resists fracture forces upon insertion and in use.

BRIEF DESCRIPTION OF THE DRAWINGS

FIGS. 4(a)-(e) respectively represent top plan, left, front, rear and bottom plan views of the implant assembly depicted in FIG. 3;

DETAILED DESCRIPTION OF THE PREFERRED EMBODIMENT(S)

The invention includes an endo-osseous anatomic dental implant assembly and its insertion process.

Figure 1:
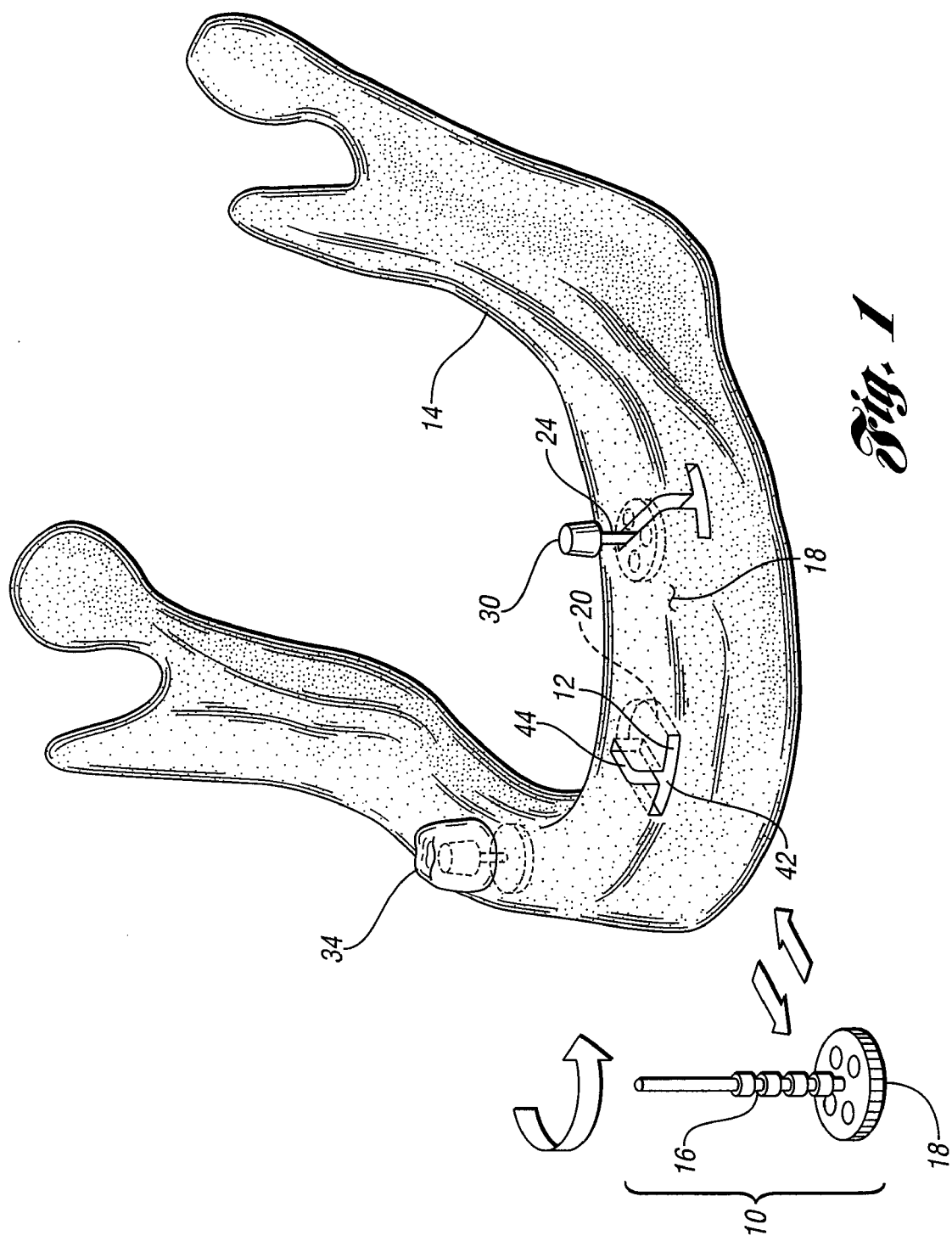
FIG. 1 is a perspective view of a lower jaw showing positioned implants, with their posts ready to receive a dental prosthesis, a representative cutting tool in operation, and an anchoring site for receiving the implant.
Figure 8:
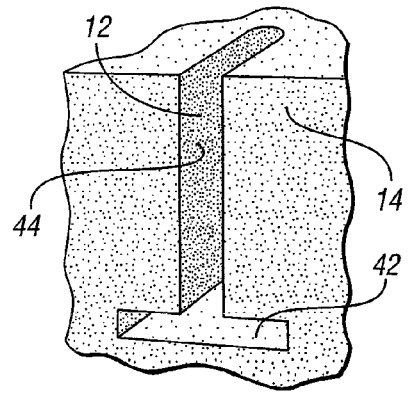
FIG. 8 depicts a slot and a tunnel of an anchoring site defined the bone which corresponds to the profile of the cutting tool.

FIG. 1 depicts representative embodiments of the invention. Energized by a rotating drill, for example, a cutting tool 10 prepares the insertion site 12 in a bone, such as a lower jaw bone 14 that receives the implant. The tool 10 includes a stem 16 that is used as a milling cutter and a disk 18 extending perpendicularly to the longitudinal axis of the stem 16. Thus, the stem 16 of tool 10 cuts the substantially vertically aligned slot 44 of the anchoring site 12, while the disk 18 defines the tunnel 42 of the anchoring site 12 (see also, FIG. 8).

Figure 2:
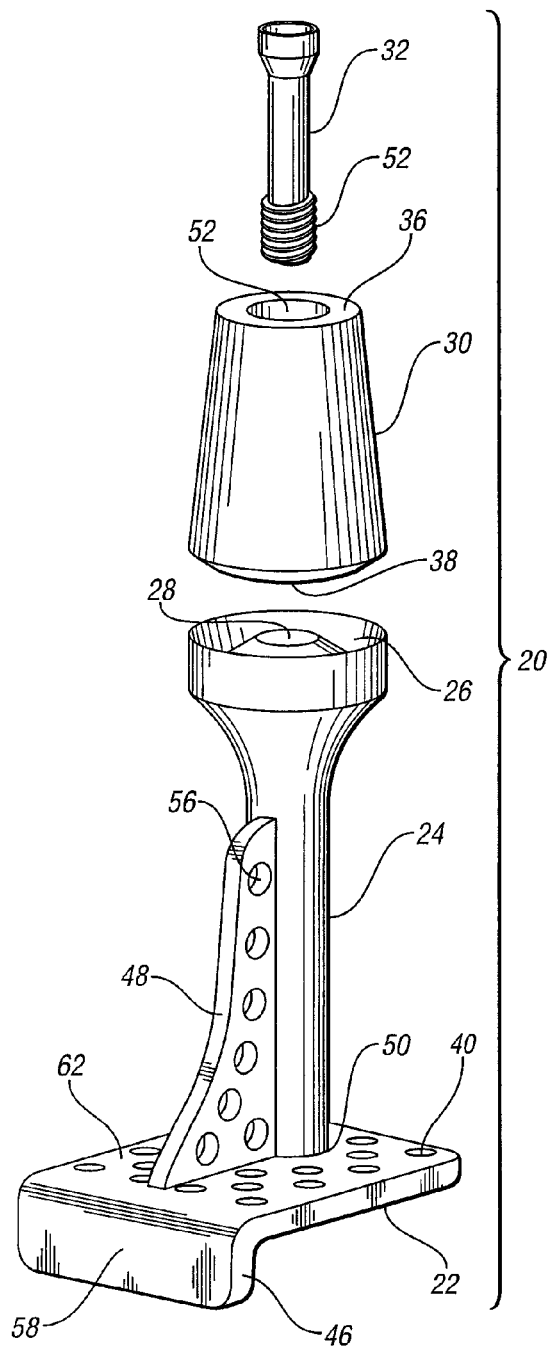
FIG. 2 is an exploded perspective view of a laterally inserted dental implant assembly for securing a dental prosthesis according to the invention.
Figure 3:
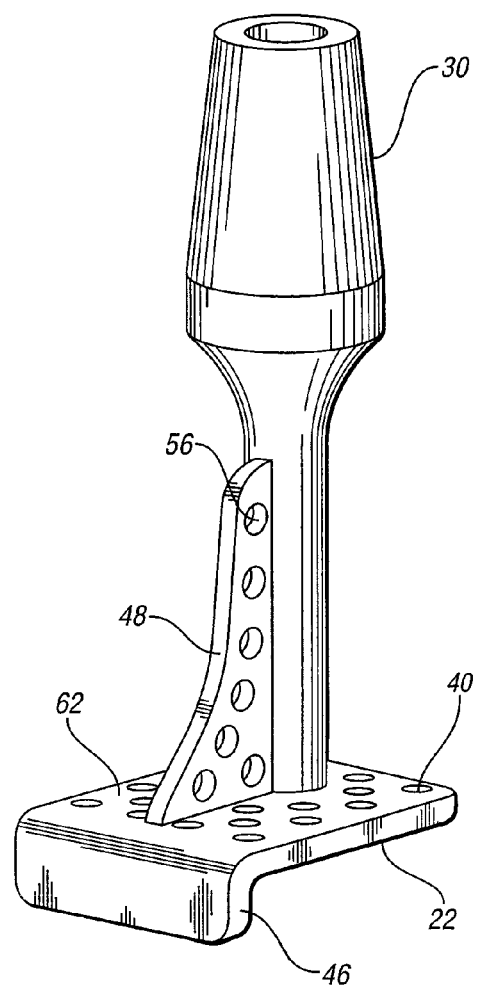
FIG. 3 depicts the dental implant assembly in its conjoined form, ready to receive the dental prosthesis.

FIGS. 2-4 depict an implant assembly 20 constructed in accordance with one embodiment of the invention. The assembly 20 has a base 22 that is preferably substantially perpendicular to the longitudinal axis of a pillar 24. The base 22 has a bone-facing surface 60 a pillar supporting surface 62, and an off-center region 64 (FIG. 4). At the opposite or distal end 26 of the pillar 24 there is a receiving device 28 which accommodates a tapped body 30 and with a through bore or a threaded post 32 on which the dental prosthesis is positioned.

As best seen in FIGS. 2 & 4, the tapped body 30 in one embodiment is defined by two truncated conical surfaces 30, 38. Major frustoconical portion 36 has a threaded post-receiving aperture that receives the threaded post 32 for supporting the tooth or the prosthetic superstructure. Minor frustoconical portion 38 has a through bore. It is contiguous with the gum and shaped to allow the gum tissue to assume the contours of its circumference. This limits the risks of irritation and retention of the bacterial plaque and food remains. The minor frustoconical portion 38 suppresses any overhanging and thus the blocks of such unwanted substances.

The base 22 of the implant assembly 20 may have multiple apertures 40 which can accommodate locking screws (not shown) to reduce the weight of the material of the implant without impairing its mechanical characteristics. Osseous tissue grows through the implant base 22 via these apertures 40 and contributes to biological blocking provided by osseous imprisonment of the base 22, the buttress 48 and the pillar 24.

In FIGS. 2-4 & 6-7 there is depicted a ledge 46 that depends downwardly by an angle theta that is preferably perpendicular to the base plate 22. If desired, apertures 58 or locking holes can be provided through the ledge 46 through which screws or pins can be inserted to secure the plate to the bone. Thus, the implant assembly 20 can be immobilized, and healing is thereby promoted.

FIGS. 2, 3, 4(a) & 6-7 illustrate that in one embodiment, the pillar 24 is located in an off-center region 64 in relation to the base plate 22. When the ledge 46 abuts the bone, the pillar 24 is able to be placed more inwardly than is possible with prior approaches. One benefit of such relocation is that the opposite distal end 26 of the pillar 24 may more closely underlie a ridge of the bone and therefore be more strongly supported.

Preferably, the buttress 48 is provided between the pillar 24 and the base plate 22, as depicted in FIGS. 2, 3, 4(a), 4(b), 4(c), 6 & 7. The buttress 48 may guide the implant assembly 20 during lateral insertion, contribute additional anchoring surfaces for bone growth, and provide mechanical support to the base plate 22 and pillar 24, thereby prolonging the useful life of the implant assembly 20.

Figure 5:
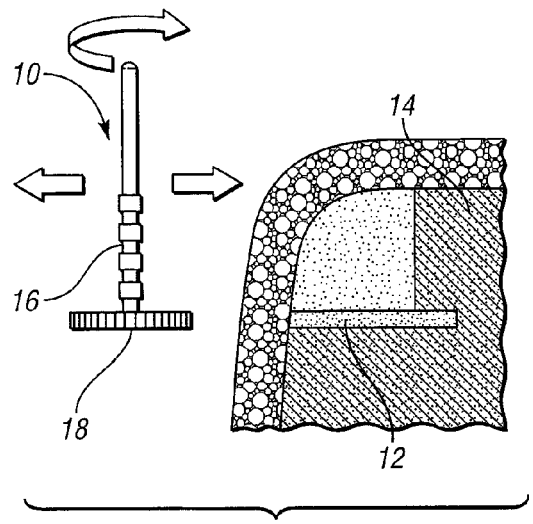
FIG. 5 shows how a cutting tool can go into and out of an anchoring site defined by a tunnel and a slot for the implant before insertion of the implant laterally into the site created by the cutting tool.
Figure 6:
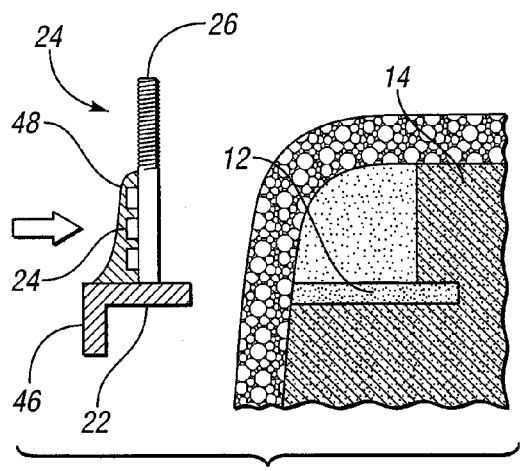
FIG. 6 depicts an implant about to be pressed into its seating tunnel and slot. The implant plate and pillar are preferably wider respectively than the slot and tunnel defined by the cutting tool, which ensures a firm grip of the implant when seated.
Figure 7:
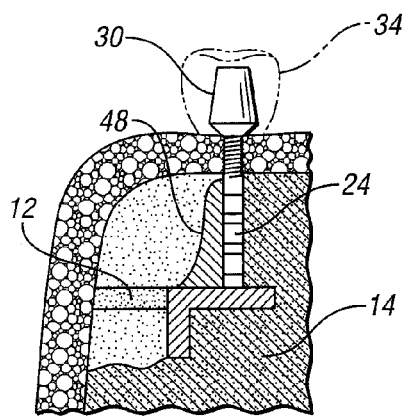
FIG. 7 is a schematic view of one embodiment of the implant in situ. A distal end of the implant pillar is equipped with a tapped body which allows a dental prosthesis to be threadingly secured or cemented thereupon.

FIG. 5 illustrates a representative cutting action of one type of tool 10 into the bone to define a site 12 for receiving the implant assembly 20. This site 12 corresponds to the profile projected laterally of the assembly 20 to be inserted generally horizontally into the site 12. Only the end 26 of pillar 24 (FIG. 6) opposite the base 22 protrudes from the edge of bone 14. FIG. 7 shows implant assembly 20 in position, firmly supporting a prosthesis 34 after the pillar 24 has been selected for the required height and has received the corresponding tapped body 30.

The base plate 22 that supports the axially extending pillar 24 is in one embodiment a quadrilateral or other polygon or disk that after insertion lies mainly disposed in a horizontal plane. In one embodiment, this plate 22 is shaped so as to be set into the mandibula or the maxilla by having side edges that are oriented on converging lines, thereby permitting a wedging interference fit upon insertion.

In use, the base plate 22 is inserted into a tunnel 42 (FIG. 8) made in the vestibular, lingual or palatal side of a bone. The pillar 24 is inserted into a slot 44—a passage that intersects the plane of the tunnel 42.

When placing the implant assembly 20 laterally against a bony wall, the practitioner, in a straight-line translation movement, allows intra- and trans-osseous penetration of the base plate 22 in a plane parallel to that of the cutting disk 18. He inserts the pillar 24 and buttress 48 in an intersecting plane that is rigidly connected to the base plate 22.

Preferably, the implant assembly 20, to be positioned correctly, has a profile that is slightly larger than the tool 10 in order to permit an interference fit into the formed tunnel 42 and slot 44.

Thus, the implant assembly 20, is placed in the tunnel 42 and slot 44 formed by the tool 10. The implant assembly 20 is inserted laterally into the site 12 preferably on the vestibular side so that only the distal end 26 of the pillar 24 opposite the base plate 22 protrudes from the bone edge (FIG. 7). The pillar 24 is selected according to the required height to receive the threaded post 32 or tapped body 30. Before its final biological blocking by regeneration of the bone around the implant 20, the implant 20 is stable.

In one embodiment, one aspect of the implant assembly 20 is identical to that of the tool 10. Others may be thicker to avoid any mobility of the implant 20 in its seated position.

Preferably, the base 22 has a smooth edge instead of being indented or grooved. The pillar 24 can be either smooth or grooved.

Thus, the implant assembly 20 according to the invention includes pillar 24 with at a distal end 26 a smooth part that interfaces with the tapped body 30 which allows threaded post 32 to be secured thereto. At the other end of the pillar 24, least one base plate 22 is placed, preferably perpendicularly to the longitudinal axis of the pillar 24.

The invention solves several problems of prior approaches. It tends to ensure a faultless primary fixation owing to the precision with which the implant is cut into the bone. The implant assembly is generally made of a metal or metallic alloy. Thus, the implant assembly 20 can be used as an artificial root in the replacement of the missing natural dental pillars.

Here are the reference numerals used and the features to which they refer.

| Reference No. | Feature |
| --- | --- |
| 10 | Tool |
| 12 | Site |
| 14 | Lower jaw bone |
| 16 | Stem of cutting tool |
| 18 | Disk |
| 20 | Implant assembly |
| 22 | Base plate |
| 24 | Pillar |
| 26 | Opposite (distal) end |
| 28 | Receiving device |
| 30 | Tapped body |
| 32 | Threaded post |
| 34 | Prosthesis post |
| 36 | Major frustoconical portion |
| 38 | Minor frustoconical portion |
| 40 | Apertures (in base) |
| 42 | Tunnel |
| 44 | Slot |
| 46 | Ledge |
| 48 | Buttress |
| 50 | Foot portion (of pillar) |
| 52 | Post receiving aperture (of 36) |
| 54 | Threaded region (of 52) |
| 56 | Apertures (in buttress) |
| 58 | Apertures (in ledge) |
| 60 | Bone-facing surface (of 22) |
| 62 | Pillar-supporting surface (of 22) |
| 64 | Off-center region (of 22) |

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A dental implant assembly for insertion into a bone, the assembly serving to support a dental prosthesis or other dental structure, the assembly including:
    a base plate having a first bone-facing surface and a second pillar-supporting surface that defines an off-center region;
    a ledge depending from the first bone-facing surface of the base plate away from the second pillar-supporting surface at an angle theta; and
    a pillar extending from the off-center region of the pillar-supporting surface of the base plate; and
    a planar buttress extending between the pillar-supporting surface of the base plate and the pillar for strengthening a connection therebetween.

2. The dental implant assembly of claim 1, wherein the pillar has a foot that is joined to the pillar-supporting end of the base plate and a flared distal end, the assembly further including:
    a receiving device located at the distal end.

3. The dental implant assembly of claim 1, additionally including:
    a tapped body having
        a minor frustoconical portion with a through bore that is seatable in the flared distal end of the pillar; and
        a major frustoconical portion extending from the minor frustoconical portion, the major frustoconical portion defining a threaded post-receiving aperture that is coaxial with the through bore.

4. The dental implant assembly of claim 3, also having:
    a post that is receivable by the post-receiving aperture, upon which a dental prosthesis may be secured.

5. The dental implant assembly of claim 4, wherein the post has a threaded region that is seatable in the post-receiving aperture.

6. The dental implant assembly of claim 1, wherein the base plate defines multiple apertures which reduce the weight of the implant assembly and permit growth therethrough of osseous tissue.

7. The dental implant assembly of claim 1, wherein the angle theta is about 90°.

8. The dental implant assembly of claim 1, wherein the ledge defines one or more apertures for screw insertion or to permit osseous growth therethrough.

9. The dental implant of claim 1, wherein the buttress defines one or more apertures for weight reduction and osseous growth.

10. The dental implant assembly of claim 1 wherein the base plate includes lateral edges that are oriented along converging lines, so that upon insertion the base plate can be wedged into a tunnel section of an anchoring receiving site.

11. A dental implant assembly kit for inserting a dental assembly into a bone, the kit comprising:
    a cutting tool, including a disk and a stem arising therefrom; the stem being securable by a rotating drill, the disk having a periphery which defines cutting edges; and
    a dental implant assembly, including a base plate, a ledge depending therefrom, from a first face thereof a pillar extending therefrom, from a second face thereof and a planar buttress that extends between the base plate and the pillar.

12. A method of positioning a dental implant, comprising cutting a slotted anchoring site in a jaw bone with a tool comprising:
    a stem having a flat cutter wheel at one end of the stem and axially oriented cutting edges in the stem, the edges extending from the flat cutter wheel,
    moving the shaft normal to its longitudinal axis so that the flat cutter wheel moves into the jaw bone,
    removing the tool from the slot, and
    emplacing in the slot an implant comprising
    a post having at one end a base plate, and a planar buttress that serves as a rudder or guide during the emplacement step said base plate having a ledge and a thickness slightly greater than that of the flat cutter wheel to wedge the implant in the jaw bone,
    the emplacing step being effected by moving the implant post normal to its axis so that the base plate of the implant may be moved laterally into the slot to conform with the jaw bone.

* * * * *